United States Patent [19]

Toder

[11] Patent Number: 4,629,074

[45] Date of Patent: Dec. 16, 1986

[54] INTRAVENOUS CONTAINER SUPPORT

[76] Inventor: Ellis I. Toder, 431 Militia Hill Rd., Fort Washington, Pa. 19034

[21] Appl. No.: 638,019

[22] Filed: Aug. 6, 1984

[51] Int. Cl.⁴ .............................................. A47G 29/00
[52] U.S. Cl. ........................................ 211/71; 248/318
[58] Field of Search ................ 211/71, 113, 162, 107; 248/318, 320, 321, 327, 328

[56] References Cited

U.S. PATENT DOCUMENTS

| | | | |
|---|---|---|---|
| 3,191,903 | 6/1965 | Wieland | 248/328 |
| 3,191,904 | 6/1965 | Karapita | 248/333 |
| 3,321,090 | 5/1967 | Greenstadt | 248/328 X |
| 4,005,844 | 2/1977 | Richmond | 248/318 X |
| 4,022,416 | 5/1977 | Kaye et al. | 248/318 |
| 4,289,244 | 9/1981 | Frankhouser | 248/318 X |

FOREIGN PATENT DOCUMENTS 1068476 11/1959 Fed. Rep. of Germany ...... 248/328

Primary Examiner—Ramon S. Britts
Assistant Examiner—Sarah A. Lechok Eley
Attorney, Agent, or Firm—Walter B. Udell

[57] ABSTRACT

An intravenous fluid container carrier including an elongated telescopic device having an outer tubular shell within which is positioned an extension rod spring loaded to retract the rod into the tubular shell, an anti-rotation device to prevent rotation of the tubular shell with respect to the extension rod, and a rod locking device to hold the extension rod locked in any position between full extension out of the shell and full retraction within the shell. The locking device is releasable by a spring loaded actuation collar surrounding the shell proximate to the lower end thereof. The upper end of the extension rod is formed with a loop for suspension from a ceiling track mounted carrier, from a wall mounted bracket, or from a floor supported stand or carrier. A pair of vertically spaced collars are locked to the tubular shell at the top and near the bottom, each collar having pivotally secured thereto four arms for carrying an intravenous fluid container, each arm being pivotable between a detented use position extending outward away from the tubular shell and a detented storage position extending closely parallel to the tubular shell.

18 Claims, 12 Drawing Figures

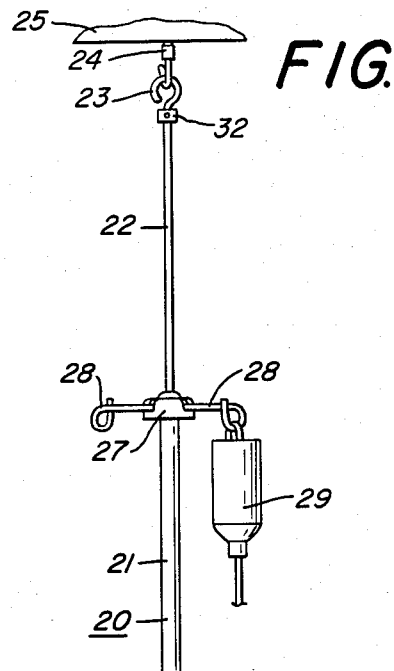
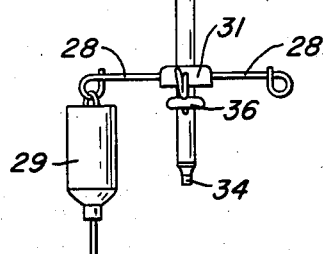
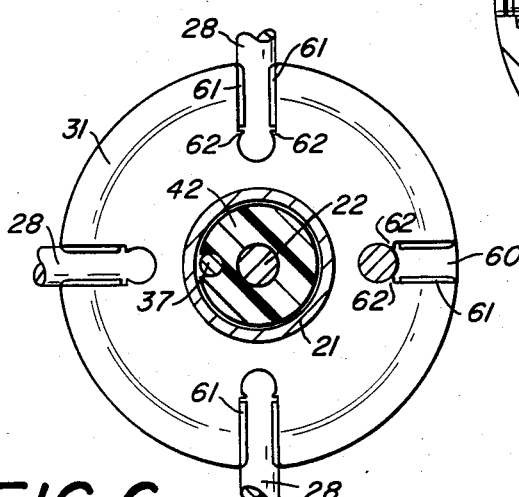
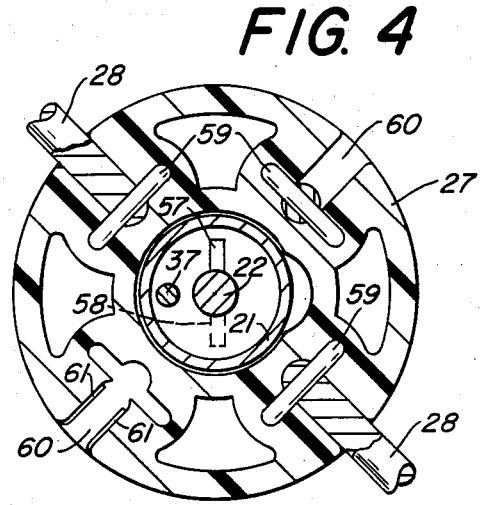
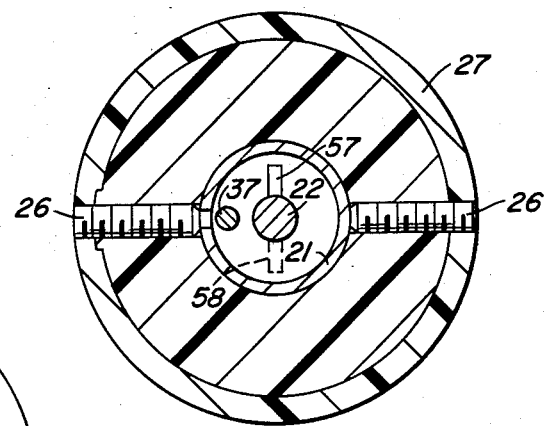

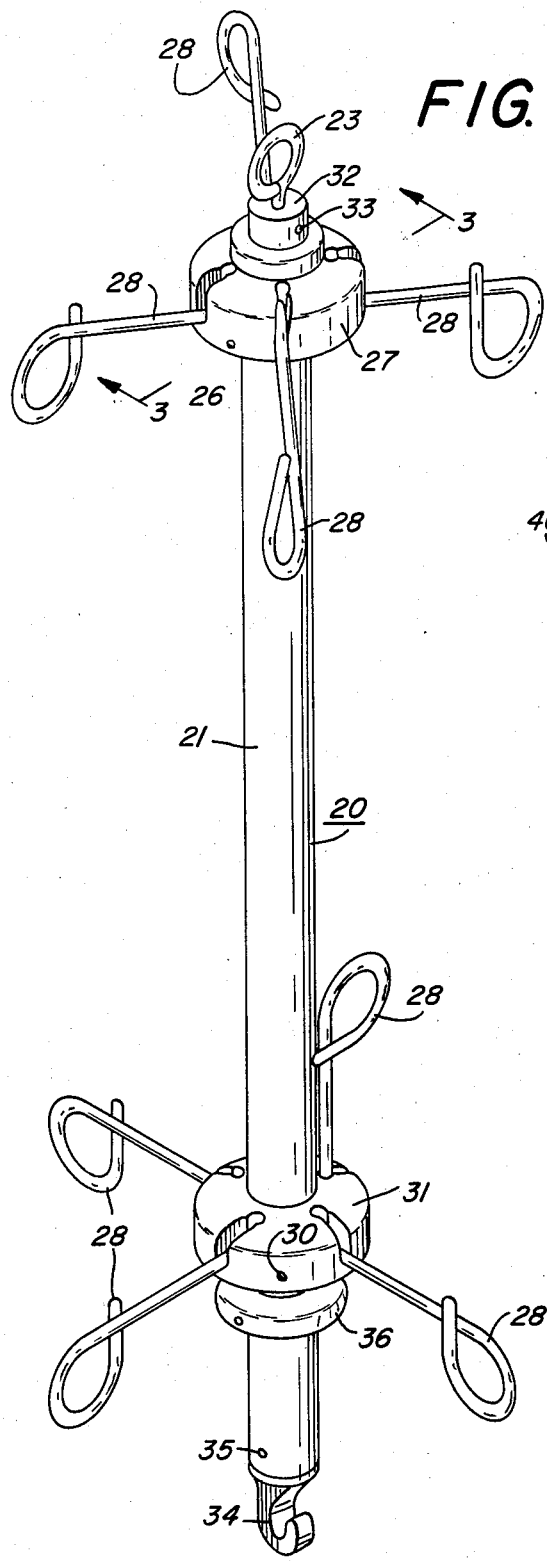
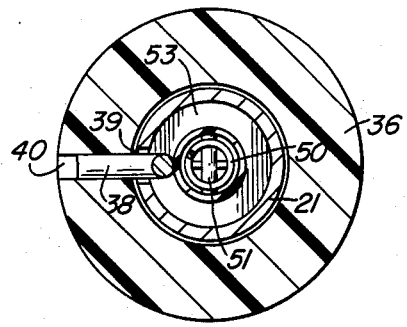
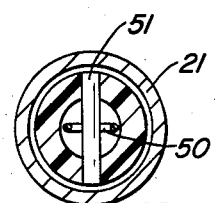
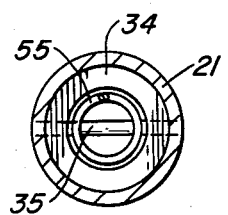

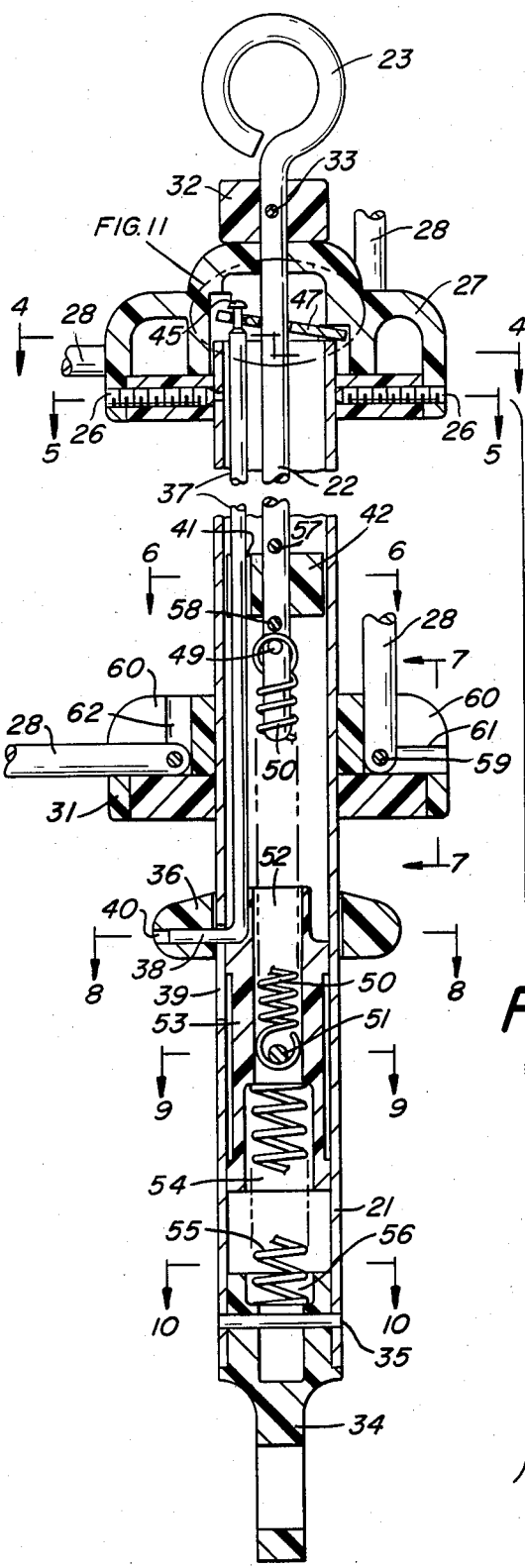
FIG. 3
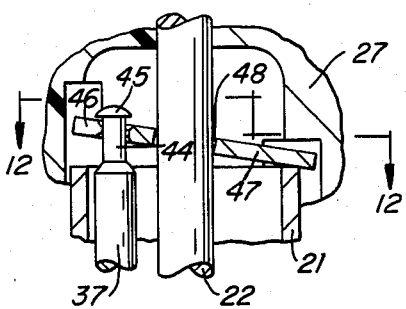
FIG. 11
FIG. 12

INTRAVENOUS CONTAINER SUPPORT

This invention relates generally to intravenous fluid container carriers such as are used in hospitals, and more particularly, relates to a novel intravenous fluid container carrier which includes a quick adjustment mechanism for vertically positioning the intravenous fluid containers, and detent devices for stabilizing the carrier arms in both storage and use positions.

The carrier according to the invention is relatively light in weight and very compact, being slim in cross sectional diameter and lengthwise contractible for ease of storage and shipment. It is made of stainless steel and plastic and can be autoclaved for sterilization. As illustrated it can hold up to nine intravenous fluid containers simultaneously. An anti-rotation feature is built into the carrier to prevent tangling of the intravenous fluid lines.

Briefly, the carrier according to the invention is an elongated telescopic device having an outer tubular shell within which is positioned an extension rod spring loaded to retract the rod into the tubular shell, and a rod locking device to hold the extension rod locked in any position between full extension out of the shell and full retraction within the shell. The locking device is releasable by a spring loaded actuating collar surrounding the shell proximate to the lower end thereof.

The upper end of the extension rod is formed with a loop for suspension from a ceiling track mounted carrier, from a wall mounted bracket, or from a floor supported stand or carrier. A pair of vertically spaced collars are locked to the tubular shell at the top and near the bottom, each collar having pivotally secured thereto four arms for carrying an intravenous fluid container, each arm being pivotable between a detented use position extending outward away from the tubular shell and a detented storage position extending closely parallel to the tubular shell.

A primary object of the invention is to provide a novel sterilizable intravenous fluid container carrier which is compact and light in weight for ease of storage and shipment.

Another object of the invention is to provide a novel carrier as aforesaid which is continuously adjustable in length to almost twice its compacted length, and which includes an anti-rotation device.

A further object of the invention is to provide a novel carrier as aforesaid including a novel length adjusting lock mechanism.

Yet another object of the invention is to provide a novel carrier as aforesaid in which the carrier arms are positively detented in both their use and storage positions.

The foregoing and other objects of the invention will become clear from a reading of the following specification in conjunction with an examination of the appended drawings, wherein:

FIG. 1 is a side elevation of the carrier in full extended position suspended from a ceiling track and shown supporting a pair of intravenous fluid containers;

FIG. 2 is a perspective of the carrier in its unextended condition and with the carrier arms in both use and storage positions;

FIG. 3 is a vertical sectional view through the carrier as would be seen when viewed on line 3—3 of FIG. 2;

FIGS. 4 through 10 are sectional views through the carrier as would be seen when viewed on the lines 4—4 through 10—10 on FIG. 3;

FIG. 11 is an enlarged fragmentary view of the extension lock which appears in the phantom elipse on FIG. 3 marked FIG. 11; and FIG. 12 is a horizontal jump section as would be seen when viewed along line 12—12 on FIG. 11.

In the several figures, like elements are denoted by like reference characters.

Referring now to the drawings, and first to FIGS. 1 and 2, there is seen the intravenous fluid container carrier according to the invention designated generally as 20 including an elongated hollow tubular shell or casing 21 within which is positioned an extension rod 22 terminating at its upper end in a hanger loop 23 supported from a track carrier 24 movable in a ceiling track 25. Secured to the upper end of the tubular shell 21 by set screws 26 is a collar 27 carrying a set of support arms 28 from one of which is carried an intravenous fluid container 29. Spaced upward a short distance from the lower end of the tubular shell 21 and secured thereto by set screws 30 is a second collar 31 carrying a second set of support arms 28 from one of which is also carried an intravenous fluid container 29. The upper end of the extension rod 22 below the hanger loop 23 passes through and is secured to a stop block 32 by means of a pin 33. The lower end of tubular shell 21 is closed by a plug hook 34 secured to the shell by a pin 35. The manually operable exterior ring 36 of the extension rod locking mechanism actuator is positioned about the lower end of the tubular shell 21 just below the lower collar 31.

Considering now FIGS. 3 through 12, and principally FIG. 3, the previously described structures are visible in somewhat more detail, as well as further views which illustrate the operation of the extension rod locking mechanism, the anti-rotation device, and the support arms detent structures. Considering first the extension rod locking mechanism and referring to FIGS. 3 and 8 through 12, there is seen an L-shaped actuating rod 37 extending through the shell 21 substantially parallel to the extension rod 22 and having a lower horizontal leg 38 extending outward through a slot 39 in the tubular shell 21 and terminating within a bore 40 in the locking actuator exterior ring 36. The actuating rod 37 extends upward within the tubular shell 21, passing loosely through a bore 41 in the guide plug 42 through which the extension rod 22 freely passes, and terminates in a reduced diameter meter neck 44 surmounted by an enlarged head 45. The neck 44 is disposed in a slot 46 in a friction lock plate 47 through a hole 48 through which passes the extension rod 2.

Held captive to the lower end of the extension rod 22 by means of pin 49 is one end of extension spring 50 the other end of which is secured by a pin 51 within a bore 52 formed in the upper end of the interior cylindrical plug portion 53 of the locking actuator. Disposed within the lower bore 54 of the locking actuator interior plug 53 is the upper end of a compression spring 55 the lower end of which is seated in a bore 56 in the upper end of plug hook 34. The compression spring 50 biases the locking actuator plug 53 upward until it is restrained from further upward movement by the lower leg 38 of the actuating rod which engages the upper end of slot 39 in the wall of tubular shell 21. The spring 50 biases the extension rod 22 downward into the interior of the tubular shell 21.

With the locking mechanism parts as shown in FIGS. 3, 11 and 12, the extension rod 22 is frictionally wedge locked by the lock plate 47 against moving upward out of the tubular shell 21, which latter is accordingly prevented from being pulled downward to lower the containers 29. In order to release the lock, the locking actuator exterior ring 36 is pulled downward which causes the actuating rod 37 to be moved downward within the tubular shell 21 to thereby pull the friction locking plate 47 down into a horizontal position. This allows the hole 48 in the lock plate to align with the extension rod 22 so that the latter and slide upward out of the shell 21 against the restraining force of extension spring 50.

At the desired extension the actuator ring 36 is released which immediately causes the friction lock plate 47 to be restored to the position shown in FIGS. 3, 11 and 12, which wedge locks the extension rod 22 against further outward movement. The extension rod 22 is withdrawn back into the tubular shell 21 with the assistance of the spring 50 by simultaneously pulling down on the actuator ring 36 and lifting the shell 21. The required lifting force is minimized by the contraction force of the extension spring 50.

The anti-rotation device is best seen in FIGS. 3 and 5 and is formed by the actuating rod 37 and pins 57 and 58 which are projected through the extension rod 22 just above and below the guide plug 42, which latter is retained in position by the pins. As best seen in FIG. 5, the pin 57, and also pin 58, does not engage the inside wall of the tubular shell 21 but is of sufficient length that a ninety degree rotation of the extension rod 22 in either direction within the shell 21 causes the pins to engage against the side of the actuating rod 37 which then prevents further rotation of the extension rod 22. This device prevents winding and unwinding of the spring 50, and tangling of the tubing leading from the intravenous fluid containers hung on the various support arms.

Referring now to FIGS. 3 through 7 for details of the support arms detent structures, it is seen that each of the support arms 28 is retained in its collar 27 or 31 by a pin 59 for pivoting movement between a support position extending outward from the tubular shell 21 and a storage position extending parallel to the tubular shell 21. As best seen in FIGS. 3, 4 and 6, each arm 28 is disposed within a channel 60 having a pair of resilient flaps or lips 61 presenting horizontally inward toward one another at an elevation above the floor of the channel equal to the diameter of the support arm. These flaps 61 are the "use position" detents and overlie a portion of the surface of the arms 28 when the arms are in their down or use position and are resiliently opened as the arms are pushed up into storage position, all as best seen in FIG. 6.

Also disposed within each channel 60, as best seen in FIGS. 3, 6 and 7, are a pair of resilient flaps or lips 62 presenting vertically inward toward one another and spaced from the inner wall of the channel at a distance equal to the diameter of the support arm. These flaps 62 are the storage position detents and embrace a portion of the surface of the arms 28 when the arms are in their up or storage position and are resiliently opened as the arms are pushed down into use position.

Having now described the invention in connection with a particularly illustrated embodiment thereof, it will be understood that modifications and variations of the invention may now naturally occur to those normally skilled in the art, and accordingly it is intended to claim the invention broadly as well as specifically as indicated by the appended claims.

What is claimed is:

1. An elongated telescopic carrier device for suspending intravenous fluid containers or the like, comprising in combination,
   (a) an elongated hollow tubular shell having upper and lower ends,
   (b) an extension rod slidably disposed within said tubular shell with one end of said rod extending out of said upper end of said tubular shell and having means thereon for suspending said device and the other end of said rod being disposed within said tubular shell,
   (c) retaining means preventing said extension rod from being completely withdrawn from said tubular shell,
   (d) locking actuator means operatively coupled to said extension rod effective when actuated in a first way to release said extension rod for movement of the latter out of and into said tubular shell, and effective when actuated in a second way to lock said extension rod at least against movement out of said tubular shell,
   (e) biasing means coupled directly to said extension rod for effectively constantly biasing said rod for movement into said tubular shell, and
   (f) support means carried by said tubular shell for suspending fluid containers therefrom.

2. A carrier device as described in claim 1 wherein said biasing means comprises a spring coupled at one place to said extension rod and coupled at another place to said locking actuator means.

3. A carrier device as described in claim 1 wherein a part of said locking actuator means is intercoupled with said tubular shell.

4. A carrier device as described in claim 1 further including anti-rotation means coupled to said extension rod effective to prevent more than a predetermined amount of relative rotation between said extension rod and said tubular shell.

5. A carrier device as described in claim 1 further including anti-rotation means coupled to said extension rod effective to prevent more than a predetermined amount of relative rotation between said extension rod and said tubular shell, said anti-rotation means when operative engaging a part of said locking actuator means.

6. A carrier device as described in claim 1 wherein said locking actuator means comprises an actuator ring extending around the periphery of said tubular shell with the plane of said ring substantially orthogonal to the longitudinal tubular axis, whereby said locking actuator means is readily actuatable from any peripheral position.

7. A carrier device as described in claim 1 wherein said locking actuator means comprises, a manually operable actuator at least a part of which is external to said tubular shell, an actuating rod at least a part of which is disposed within said tubular shell and which is coupled to said manually operable actuator, and a lock plate coupled to said actuating rod and releasably lockingly engaged with said extension rod, said lock plate being released from locking engagement with said extension rod by said actuating rod when said manually operable actuator is actuated in a first way.

8. A carrier device as described in claim 1 wherein said locking actuator means comprises, a manually operable actuator at least a part of which is external to said tubular shell, an actuating rod at least a part of which is disposed within said tubular shell and which is coupled to said manually operable actuator, and a lock plate coupled to said actuating rod and releasably lockingly engaged with said extension rod, said lock plate being released from locking engagement with said extension rod by said actuating rod when said manually operable actuator is actuated in a first way, said manually operable actuator comprising an actuator ring extending around the periphery of said tubular shell with the plane of said ring substantially orthogonal to the longitudinal tubular axis, whereby said locking actuator means is readily actuatable from any peripheral position.

9. A carrier device as described in claim 1 wherein a part of said locking actuator means is intercoupled with said tubular shell, and wherein said biasing means comprises a spring coupled at one place to said extension rod and coupled at another place to said locking actuator means.

10. A carrier device as described in claim 1 wherein a part of said locking actuator means is intercoupled with said tubular shell, and wherein said biasing means comprises a spring coupled at one place to said extension rod and coupled at another place to said locking actuator means, and further including anti-rotation means coupled to said extension rod effective to prevent more than a predetermined amount of relative rotation between said extension rod and said tubular shell.

11. A carrier device as described in claim 1
    (a) wherein a part of said locking actuator means is intercoupled with said tubular shell,
    (b) wherein said biasing means comprises a spring coupled at one place to said extension rod and coupled at another place to said locking actuator means,
    (c) wherein said locking actuator means comprises a manually operable actuator at least a part of which is external to said tubular shell, an actuating rod at least a part of which is disposed within said tubular shell and which is coupled to said manually operable actuator, and a lock plate coupled to said actuating rod and releasably lockingly engaged with said extension rod, said lock plate being released from locking engagement with said extension rod by said actuating rod when said manually operable actuator is actuated in a first way, and
    (d) further including anti-rotation means coupled to said extension rod effective to prevent more than a predetermined amount of relative rotation between said extension rod and said tubular shell.

12. A carrier device as described in claim 1
    (a) wherein a part of said locking actuator means is intercoupled with said tubular shell,
    (b) wherein said biasing means comprises a spring coupled at one place to said extension rod and coupled at another place to said locking actuator means,
    (c) wherein said locking actuator means comprises, a manually operable actuator at least a part of which is external to said tubular shell, an actuating rod at least a part of which is disposed within said tubular shell and which is coupled to said manually operable actuator, and a lock plate coupled to said actuating rod and releasably lockingly engaged with said extension rod, said lock plate being released from locking engagement with said extension rod by said actuating rod when said manually operable actuator is actuated in a first way, said manually operable actuator comprising an actuator ring extending around the periphery of said tubular shell with the plane of said ring substantially orthogonal to the longitudinal tubular axis, whereby said locking actuator means is readily actuatable from any peripheral position, and
    (d) further including anti-rotation means coupled to said extension rod effective to prevent more than a predetermined amount of relative rotation between said extension rod and said tubular shell, said anti-rotation means when operative engaging a part of said locking actuator means.

13. A carrier device as described in claim 1 wherein said support means carried by said tubular shell for suspending fluid containers therefrom comprises a plurality of support arms swingably coupled to said tubular shell for movement between a use position in which said arms extend outward away from said tubular shell and a storage position in which said arms lie substantially parallel to and closely alongside of said tubular shell.

14. A carrier device as described in claim 1 wherein said support means carried by said tubular shell for suspending fluid containers therefrom comprises,
    (a) a plurality of support arms swingably coupled to said tubular shell for movement between a use position in which said arms extend outward away from said tubular shell and a storage position in which said arms lie substantially parallel to and closely alongside of said tubular shell, and
    (b) detent means effective to releasably latch said support arms in said position.

15. A carrier device as described in claim 1 wherein said support means carried by said tubular shell for suspending fluid containers therefrom comprises,
    (a) a plurality of support arms swingably coupled to said tubular shell for movement between a use position in which said arms extend outward away from said tubular shell and a storage position in which said arms lie substantially parallel to and closely alongside of said tubular shell, and
    (b) detent means effective to releasably latch said support arms in said storage position.

16. A carrier device as described in claim 1 wherein said support means carried by said tubular shell for suspending fluid containers therefrom comprises,
    (a) a plurality of support arms swingably coupled to said tubular shell for movement between a use position in which said arms extend outward away from said tubular shell and a storage position in which said arms lie substantially parallel to and closely alongside of said tubular shell,
    (b) detent means effective to releasably latch said support arms in said use position, and
    (c) detent means effective to releasably latch said support arms in said storage position.

17. A carrier device as described in claim 12 wherein said support means carried by said tubular shell for suspending fluid containers therefrom comprises,
    (a) a plurality of support arms swingably coupled to said tubular shell from movement between a use position in which said arms extend outward away from said tubular shell and a storage position in which said arms lie substantially parallel to and closely alongside of said tubular shell,
    (b) detent means effective to releasably latch said support arms in said use position, and
    (c) detent means effective to releasably latch said support arms in said storage position.

18. A carrier device as described in claim 16 wherein said detent means are formed from resilient material which at least partially surrounds a region of each said support arm proximate to the region where each said arm is swingably coupled to said tubular shell.

* * * * *